United States Patent [19]

Fulton et al.

[11] Patent Number: 4,810,392
[45] Date of Patent: Mar. 7, 1989

[54] SAMPLE DISPENSING SYSTEM FOR LIQUID CHROMATOGRAPHY

[75] Inventors: Scott P. Fulton, Brookline; Douglas B. Tiffany, Danvers, both of Mass.

[73] Assignee: W. R. Grace & Co., Lexington, Mass.

[21] Appl. No.: 134,401

[22] Filed: Dec. 17, 1987

Related U.S. Application Data

[62] Division of Ser. No. 40,440, Apr. 17, 1987, Pat. No. 4,734,190.

[51] Int. Cl.⁴ ............................................. B01D 15/08
[52] U.S. Cl. ................................ 210/659; 210/656; 417/392; 417/401; 55/67
[58] Field of Search ............... 417/323, 390, 392, 401; 210/656, 659, 101, 198.2; 55/67, 386

[56] References Cited

U.S. PATENT DOCUMENTS 4,681,678  7/1987  Leaseburge ..................... 216/198.2
4,684,465  8/1987  Leaseburge ..................... 210/198.2

*Primary Examiner*—Ernest G. Therkorn
*Attorney, Agent, or Firm*—Stacey L. Channing; William L. Baker

[57] ABSTRACT

A method and apparatus for supplying a preset amount of sample solution to a liquid chromatographic column wherein (1) a first piston, which moves along the axis of a piston container sealingly contacting the side walls of said piston container, is moved a preset distance so as to draw a fixed amount of driving solution from the driving solution chamber of a piston cylinder into the piston container, thus displacing a second piston which moves along the axis of said piston cylinder sealingly contacting the side walls of said piston cylinder and dividing said piston cylinder into a sample solution chamber and a driving solution chamber, said displacement of said second piston serving to cause sample solution to be drawn from a sample solution reservoir into the sample solution chamber of the piston cylinder in a fixed amount equal to the fixed amount of driving solution drawn into the piston container; and (2) driving solution is pumped into said driving solution chamber in order to displace said second piston so that sample solution in the sample solution chamber is forced out of the sample solution chamber and onto said chromatographic column.

17 Claims, 4 Drawing Sheets

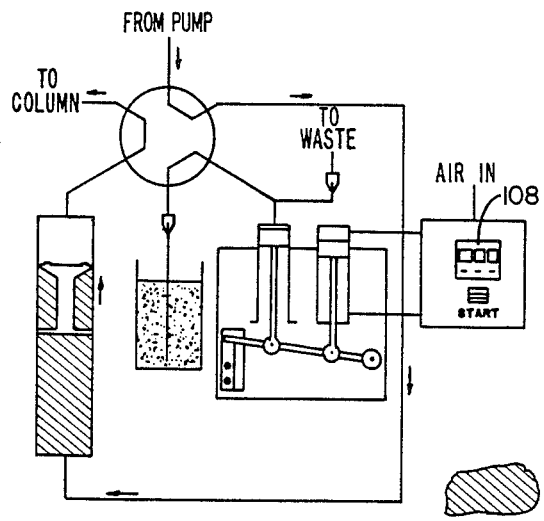
FIG. 2a PRIMING
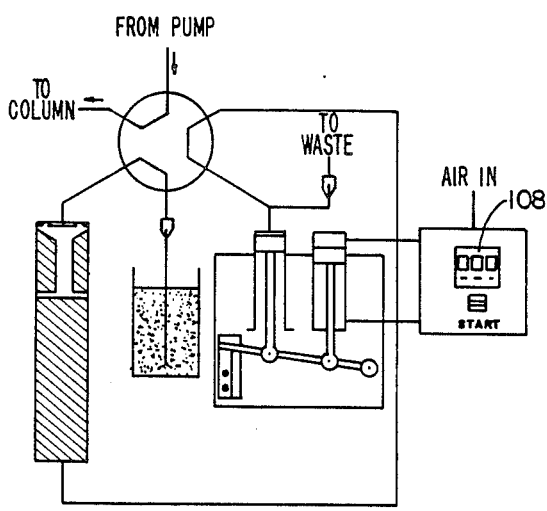
FIG. 2b STANDBY
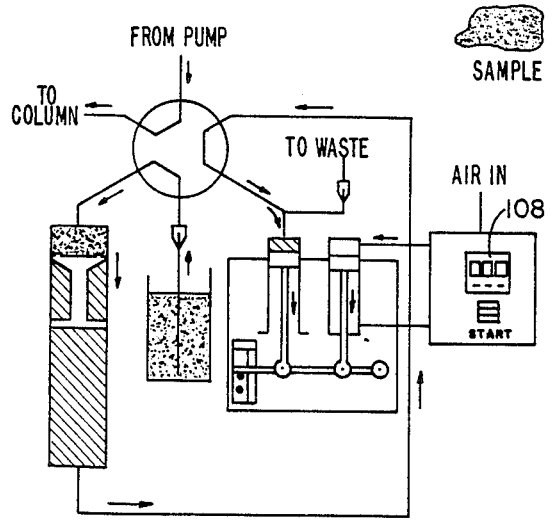
FIG. 2c FILL INTAKE
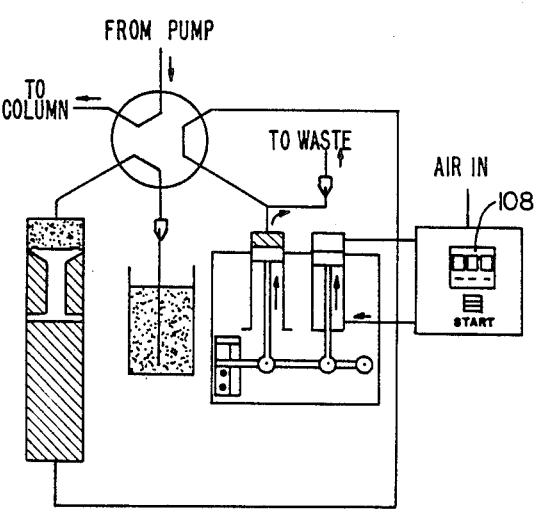
FIG. 2d FILL EJECT
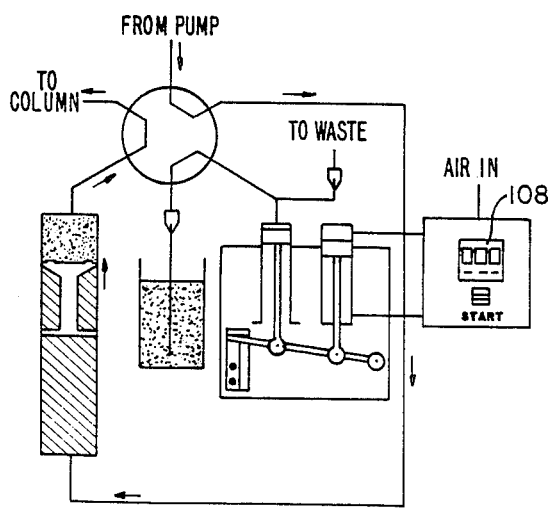
FIG. 2e INJECT SAMPLE
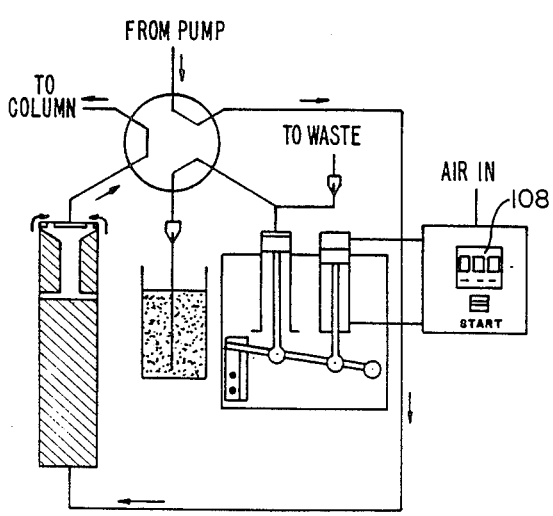
FIG. 2f FLUSH

SAMPLE DISPENSING SYSTEM FOR LIQUID CHROMATOGRAPHY

This is a division of application Ser. No. 040,440, filed Apr. 17, 1987, now U.S. Pat. No. 4,734,190

BACKGROUND OF THE INVENTION

The invention relates to an automated method and an apparatus for filling a piston cylinder with a variable but preset amount of sample solution and then discharging the sample solution from said piston cylinder onto a liquid chromatographic column.

Liquid chromatography is a well known separation technique which is utilized for separating various components contained in a sample. In the practice of liquid chromatography, it has been the custom to feed a measured amount of a sample solution containing a mixture of components needing to be separated to the top of a fractionation column of a chromatography material, e.g. gel particles, and then a suitable mobile phase (driving solution) is allowed to pass through the column, bringing with it components contained in the sample solution. The various components of the sample solution will, depending upon different degrees of interaction with the chromatography material, pass through the column at different speeds, thereby making it possible to separate the various components of the sample from each other.

A prerequisite for obtaining optimal results in liquid chromatographic separation is that the sample has to be applied on the column correctly. A common method of applying the sample solution onto the column is to apply the desired amount by means of an injection syringe. This manual method has obvious limitations.

Another prerequisite for obtaining optimal results in liquid chromatographic separation is that any appreciable intermixing of sample solution with driving solution prior to fractionation of the sample solution on the column should be avoided. If any appreciable intermixing of the sample solution with the driving solution occurs before actual fractionating of the sample solution on the column, such intermixing causes the separation bands to be fuzzy or to result in "tailing".

One method and apparatus for applying a variable but preset amount of sample solution to a chromatographic column is taught in U.S. Pat. No. 4,389,316 which makes use of a sample container of uniform cross-section, which by means of a piston is divided into a driving solution chamber and a sample solution chamber. The piston is slideable in the tubular container while sealing against the container wall so that the two chambers normally do not communicate with each other. Sample solution may be drawn into the sample solution chamber by moving the piston upwards in said sample container via a control handle attached to the piston rod which is attached to the piston. Said sample container may be marked with gradations so that the piston can be moved a preset amount in order to permit a fixed amount of sample solution to enter the sample solution chamber. Driving solution is then pumped into the driving solution chamber and this displaces the piston, thus discharging said fixed amount of sample solution to the chromatographic column. A few disadvantages to this method and apparatus are (1) difficulty of automation; (2) inability to vary the preset fixed amount of sample solution by small increments; (3) difficulty of providing a high pressure (e.g. 2000 psi) sliding seal to the outside, etc.

It is therefore an object of the invention to provide an automated method and apparatus for supplying a preset amount of sample solution to a liquid chromatographic column.

It is a further object of the invention to provide such a method and apparatus in which the preset amount of sample solution can be varied by small increments.

It is still a further object of the invention to provide such a method and apparatus in which any appreciable intermixing of sample solution with driving solution prior to fractionation of the sample solution on the column is avoided.

These and other advantages are obtained in accordance with the invention by means of the method and the apparatus for sample application defined in the following claims and described in more detail below.

BRIEF DESCRIPTION OF THE DRAWING

FIGS. 2 $a,b,c,d,e$ and $f$ are schematic diagrams illustrating one embodiment of the sample application method according to the invention.

SUMMARY OF THE INVENTION

Figure 1:
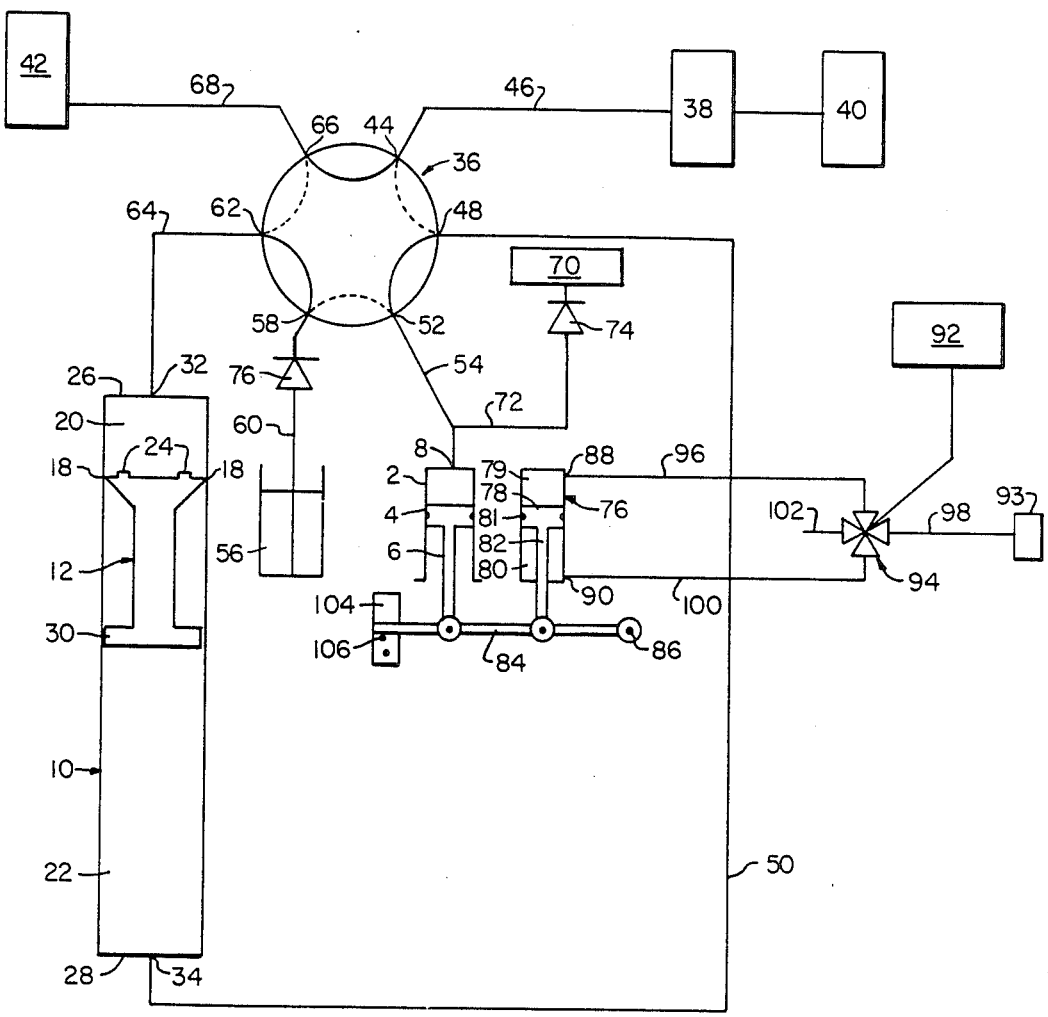
FIG. 1 is a schematic view of one embodiment of the apparatus of the invention.

The objects of the invention are accomplished by a method and apparatus for supplying a preset but variable amount of sample solution to a liquid chromatographic column in which (1) a first piston, which moves along the axis of a piston container sealingly contacting the side walls of said piston container, is moved a preset distance so as to draw a fixed amount of driving solution from the driving solution chamber of a piston cylinder into the piston container, thus displacing a second piston which moves along the axis of said piston cylinder sealingly contacting the side walls of said piston cylinder and dividing said piston cylinder into a sample solution chamber and a driving solution chamber, said piston cylinder having a sample solution chamber end and a driving solution chamber end, said displacement of said second piston serving to cause sample solution to be drawn from a sample solution reservoir into the sample solution chamber of the piston cylinder in a fixed amount equal to the fixed amount of driving solution drawn into the piston container and (2) driving solution is pumped into said driving solution chamber in order to displace said second piston so that sample solution in the sample solution chamber is forced out of the sample solution chamber and onto said chromatographic column. Prior to pumping driving solution into said driving solution chamber, there preferably is a further step of moving the first piston back to its initial position, the driving solution in said piston container being expelled to waste. The steps of moving the first piston a preset distance and then moving the first piston back to its initial position as described above, are repeated in sequence as many times as necessary until the desired amount of sample solution to be loaded onto the chromatographic column is obtained in the sample solution chamber.

In order to be able to vary the preset amount of sample solution by small increments, the diameter of the piston container is preferably less than the diameter of the piston cylinder and more preferably is less than or equal to half the diameter of the piston cylinder. Preferably, the volume capacity of the piston container is less than the volume capacity of the piston cylinder. The means for moving the first piston preferably comprises a pneumatic system, since a pneumatic system would be explosionproof. The second piston preferably comprises a freely movable piston and there preferably are stop means, either attached to said second piston or to said sample solution chamber end of the piston cylinder, which prevent said second piston from contacting the sample solution chamber end of the piston cylinder. Furthermore, there preferably is a flexible sliding seal around the second piston that enables said second piston to sealingly contact the side walls of said piston cylinder and which sliding seal bends under pressure to allow driving solution from the driving solution chamber to enter the sample solution chamber when said stop means attached to said second piston contacts the sample solution chamber end of the piston cylinder or when the second piston contacts the stop means attached to the sample solution chamber end of the piston cylinder.

DESCRIPTION OF THE PREFERRED EMBODIMENT

Figure 3:
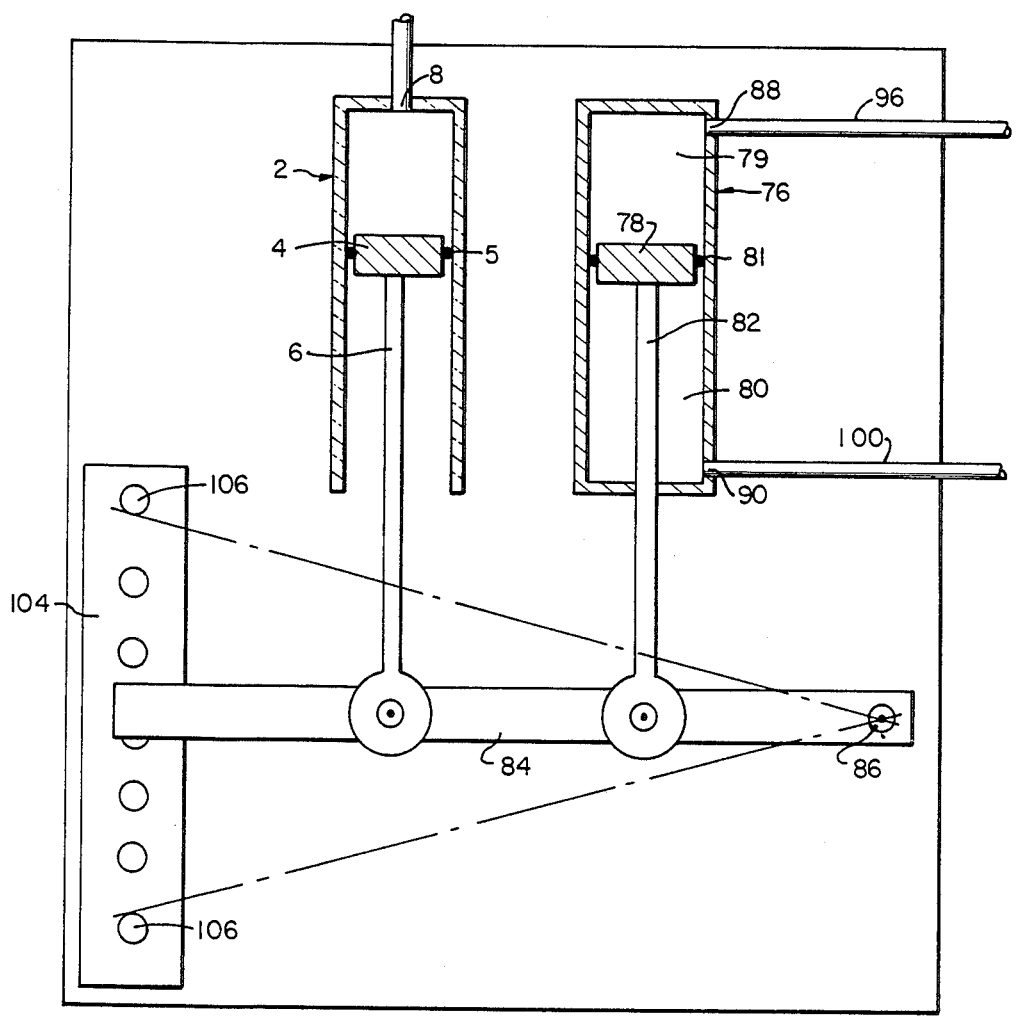
FIG. 3 illustrates a portion of one embodiment of a pneumatic system of the invention.

Referring to FIGS. 1,2 and 3, piston container 2, having uniform cross section, is provided with piston 4 which is adapted to move along the axis of piston container 2 sealingly contacting the side walls of piston container 2. One way of forming said sliding seal, as shown in FIG. 3, would be to use an O-ring 5 around piston 4. Another way of forming said sliding seal would be to machine piston 4 in such a way that there would be a tight fit between piston 4 and piston container 2. Piston 4 is connected to a piston rod 6. Piston container 2 is preferably a commercial glass syringe with a Teflon ® (polytetrafluoroethylene material obtained from E. I. duPont de Nemours & Co.) plunger in which the sliding seal is formed by a tight fit. Piston container 2 has a passageway 8 at one end of the introduction and removal of driving solution, the other end of piston container 2 being open to the atmosphere.

What is meant here by container is a structure that has side walls and two ends, one end of which is open to the atmosphere. This is to be distinguished from cylinder which refers to a structure that has side walls and two ends, neither end of which is open to the atmosphere.

Figure 4:
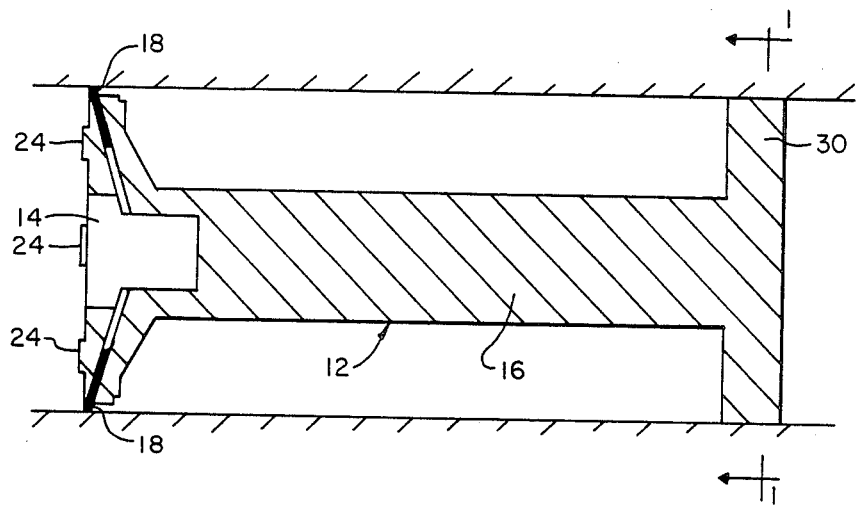
FIG. 4 illustrates one embodiment of the piston which divides the piston cylinder into a sample solution chamber and a driving solution chamber.
Figure 5:
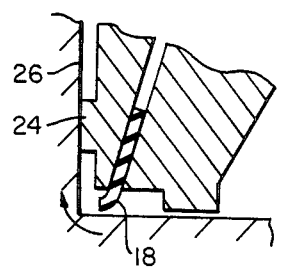
FIG. 5 is an enlarged view of the portion of the piston of FIG. 4 with the flexible sliding seal.
Figure 6:
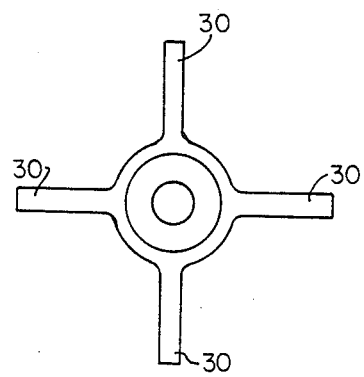
FIG. 6 is a sectional view taken along line 1—1 of FIG. 4 of the legs of said piston.

Piston cylinder 10, having uniform cross section, is provided with a freely movable piston 12 which is adapted to move along the axis of piston cylinder 10 sealingly contacting the side walls of piston cylinder 10 and dividing said piston cylinder into a sample solution chamber 20 and a driving solution chamber 22, said piston cylinder 10 having two ends, a sample solution chamber end 26 and a driving solution chamber end 28. When pressure is applied to either the sample solution chamber 20 or the driving solution chamber 22, piston 12 moves freely in the direction of the pressure. As seen more clearly in FIGS. 4 and 5, piston 12 is formed from a piston face 14 and piston body 16 which are attached together with a seal 18, formed of a flexible material (such as rubber or Kalrez ®- obtained from E. I. duPont de Nemours & Co.), sandwiched between. The seal 18 is of such a dimension as to rub against piston cylinder 10 and normally serves to prevent intermixing between liquid in the sample solution chamber 20 and driving solution chamber 22. Nubs 24 are attached to said piston face 14 to prevent piston 12 from contacting the sample solution chamber end 26 of piston cylinder 10. Instead of having nubs 24 attached to the piston face 14, nubs could be attached to the sample solution chamber end 26 of the piston cylinder 10 to prevent piston 12 from contacting the sample solution chamber end 26 of piston cylinder 10. At least one nub, but preferably more, is preferably attached either to piston 12 or to sample solution chamber end 26 to prevent piston 12 from contacting the sample solution chamber end 26 of piston cylinder 10. When the piston 12 reaches the sample solution chamber end 26, the nubs 24 prevent direct contact between piston 12 and the sample solution chamber end 26, but prevent piston 12 from making any further movement. The high pressure drop that thus develops across the seal 18 forces the flexible seal 18 to bend, as shown in FIG. 5, thus opening a space between the seal 18 and the side walls of piston cylinder 10 and allowing driving solution from the driving solution chamber 22 to enter the sample solution chamber 22. As seen in FIG. 6, the piston body 16 has four legs 30 to allow free flow of liquid around the piston body 16, but maintain proper alignment of the piston 12 in the piston cylinder 10. Sample solution chamber 20 has a passageway 32 for the introduction and removal of sample solution and driving solution chamber 22 has a passageway 34 for the introduction and removal of driving solution.

An adjustable valve 36, which is preferably a 2 position 6 port valve as shown in FIG. 1, is adjustable between a sample application position and an elution position. The broken connection lines in the valve 36 in FIG. 1 mark the sample application position, whereas the unbroken (solid) connection lines mark the elution position. The adjustment of valve 36 between the two positions can be made manually, but is preferably performed by a control unit which automatically resets the valve 36. A pump 38 for pumping driving solution from a driving solution reservoir 40 into driving solution chamber 22 and for pumping driving solution from driving solution reservoir 40 onto chromatographic column 42 is connected to port 44 of said valve 36 via conduit 46. Passageway 34 of driving solution chamber 22 is connected to port 48 of valve 36 via conduit 50. Passageway 8 of piston container 2 is connected to port 52 of valve 36 via conduit 54. A sample solution reservoir 56 is connected to port 58 of valve 36 via conduit 60. Passageway 32 of sample solution chamber 20 is connected to port 62 of value 36 via conduit 64. Chromatographic column 42 is connected to port 66 of value 36 via conduit 68. Thus, valve 36 serves to interconnect pump 38 with driving solution chamber 22, driving solution chamber 22 with piston container 2, piston container 2 with sample solution reservoir 56, sample solution reservoir 56 with sample solution chamber 20, sample solution chamber 20 with chromatographic column 42 and chromatographic column 42 with pump 38. In the elution application position shown in unbroken connection lines in FIG. 1, the pump 38 pumps driving solution to the chromatographic column 42, and by moving piston 4 down a preset distance, a fixed amount of driving solution is drawn from driving solution chamber 22 into piston container 2, thus displacing piston 12 downward, the displacement of piston 12 downward serving to draw sample solution from the sample solution reservoir 56, in a fixed amount equal to the fixed amount of driving solution drawn into piston container 2, into the sample solution chamber 20. In the sample application position shown in broken connection lines in FIG. 1, the pump 38 pumps driving solution to driving solution chamber 22 which displaces piston 12 upwards, thus serving to force sample solution in the sample solution chamber 20 (or driving solution which has entered the sample solution chamber 20 as a result of the bending of flexible seal 18 due to pressure) onto chromatographic column 42.

If it is desired to load more sample solution onto the chromatographic column 42 than that obtained in sample solution chamber 20 by virtue of moving piston 2 down a preset distance once, then a waste container of any form 70 is connected to piston container 2. One way of connecting waste container 70 to piston container 2 would be via conduit 72, which conduit 72 could be connected to conduit 54, as shown in FIG. 1, by some means such as a T joint, thus passageway 8 of piston container 2 would be connected to waste container 70 via conduit 54 and conduit 72. If piston container 2 was connected to waste container 70 via a conduit, then it would be necessary for said conduit, conduit 72 in FIG. 1, to have a check valve 74 (check valve by definition only allows flow in one direction) to ensure that solution cannot flow from waste container 70 to piston container 2 and there would need to be a check valve, such as check valve means 76 on conduit 60, to ensure that driving solution from piston container 2 only flows to the wast container. Although this latter check valve could have been located, for example, on conduit 54 above the juncture of conduits 54 and 72, by having check valve 76 located on conduit 60, it serves a dual function of ensuring that driving solution from piston container 2 only flows into waste container 70 and that driving solution cannot flow into sample solution reservoir 56 when valve 36 is reset to the eluent position. Another way of connecting waste container 70 to piston container 2 (not shown) would be to have a valve, e.g. a 3 way valve, on conduit 54 connected to the waste container via a conduit and a controlling means to control the opening and closing of the valve ports of said valve.

The system illustrated in FIGS. 1 and 2, can according to the invention be used in the following way. First, the driving solution chamber 22 of the piston cylinder 10 is filled with driving solution, e.g. a buffer solution or other type of solution depending on the nature of the sample solution. This can be done as shown in FIG. 2a by setting valve 36 to the sample application position so that pump 38 can pump driving solution from driving solution reservoir 40 to driving solution chamber 22. By pumping driving solution into driving solution chamber 22, piston 12 is moved upward. As described previously, when piston 12 has been moved upward enough that nubs 24 on piston 12 contact the sample solution chamber end 26, the flexible seal 18 bends and driving solution from the driving solution chamber 22 enters the sample solution chamber 22 and can go from there into conduit 64, conduit 68 and chromatographic column 42.

After the driving solution chamber 22 of piston cylinder 10 is filled with driving solution, driving solution is preferably pumped into chromatographic column 42 in order to equilibrate column 42. This can be done, as seen in FIG. 2b, by setting valve 36 to its second position, the eluent position, and using pump 38 to pump driving solution from driving solution reservoir 40 directly to column 42.

Next, with valve 36 in the eluent position as seen in FIG. 2c, piston 4 is moved downward from the top of piston container 2 a preset amount in piston container 2, creating suction so that a fixed amount of driving solution is drawn from driving solution chamber 22 into piston container 2 through passageway 8. The reduced pressure in conduit 72 caused by the movement down of piston 4 serves to close check valve 74 more tightly. This decrease in the amount of driving solution in driving solution chamber 22 causes freely movable piston 12 to be displaced downward, creating suction so that check valve 76 opens and sample solution from sample solution reservoir 56 is drawn into sample solution chamber 20 in a fixed amount equal to the fixed amount of driving solution drawn into piston container 2. As seen in FIG. 2c, while the sample solution is being drawn into sample solution chamber 20, pump 38 can be pumping driving solution from driving solution reservoir 40 to chromatographic column 42.

If no more sample solution, other than the sample solution obtained in sample solution chamber 20 as a result of moving piston 4 down a preset distance once, is desired to be loaded on chromatographic column 42, then valve 36 is set to its sample application position, as seen in FIG. 2e and pump 38 pumps driving solution from driving solution reservoir 40 into driving solution chamber 22, thus displacing piston 12 upwards and serving to discharge sample solution from sample solution chamber 20 onto chromatographic column 42.

However, if more sample solution than the sample solution obtained in sample solution chamber 20 as a result of moving piston 4 down a preset distance once is desired to be loaded on chromatographic column 42, then with valve 36 in the eluent position, piston 4 is moved upward to its initial position as seen in FIG. 2d. This movement of piston 4 upwards causes an increase in pressure in conduits 54, 50, 64 and 70, thus serving to close check valve 76 more tightly and to open check valve 74 so that driving solution from piston container 2 is discharged into waste container 70. The above-described steps of moving piston 4 down a preset amount in order to obtain a fixed amount of sample solution in sample solution chamber 20 and moving piston 4 back up to its initial position at the top of piston container 2 in order to expel driving solution in piston container 2 to waste are repeated in sequence as many times as necessary until the desired amount of sample solution to be loaded onto chromatographic column 42 is obtained in sample solution chamber 20.

After the desired amount of sample solution to be loaded onto column 42 is obtained in sample solution chamber 20, then as above-discussed, valve 36 is set to its sample application position, as seen in FIG. 2e, and pump 38 pumps driving solution from driving solution reservoir 40 into driving solution chamber 22, thus displacing piston 12 upwards and serving to discharge sample solution from sample solution chamber 20 onto column 42. As seen in FIG. 2f, once piston 12 has been moved upward enough that nubs 24 on piston 12 contact the sample solution chamber end 26, the flexible seal 18 bends and driving solution from driving solution chamber 22 enters the sample solution chamber 20 and forces any remaining sample solution in sample solution chamber 20 onto the column 42.

Once all the sample solution in sample solution chamber 20 has been discharged onto chromatographic column 42, the supply of driving solution to the driving solution chamber 22 is interrupted, e.g. by setting valve 36 to its eluent position, and driving solution is then pumped directly to the chromatographic column in order to elute sample components from the column, e.g. by pumping driving solution from driving solution reservoir 40 directly to chromatographic column 42.

Although any means for moving piston 4 a preset amount in piston container 2 will do, the means for moving piston 4 in piston container 2 preferably comprises a pneumatic system. As seen in FIGS. 1, 2 and 3, the pneumatic system preferably comprises an air cylinder 76, having uniform cross section, which is provided with piston 78, piston 78 being adapted to move along the axis of air cylinder 76 sealingly contacting the side walls of air cylinder 76 and dividing air cylinder 76 into chamber 79 and chamber 80. One way of forming said sliding seal, as seen in FIG. 3, would be to use an O-ring 81 around piston 78. Piston 78 is connected to piston 4 through the open end of piston container 2. As seen in FIGS. 1, 2 and 3, the preferred way to connect piston 78 to piston 4 is to connect piston rod 82, which is connected at one end to piston 78, to a lever arm 84 at the other end of piston rod 82 and to connect piston rod 6, which is connected at one end to piston 4, to lever arm 84 at the other end of piston rod 6. Lever arm 84 has a pivot 86 preferably located at one end of the lever arm 84 which allows lever arm 84 to pivot.

Said preferable pneumatic system further comprises passageway 88 for the introduction of air to chamber 79 of air cylinder 76; passageway 90 for the introduction of air to chamber 80 of air cylinder 76; a means for supplying air into cylinder 76 through passageways 88 and 90; and a controlling means 92 for controlling the supply of air to passageways 88 and 90. One suitable means for supplying air into air cylinder 76 through passageways 88 and 90 comprises air pumping means 93 and a valve 94 which interconnects air pumping means 93 to passageways 88 and 90. Valve 94 is preferably a four port valve with passageway 88 being connected to one port via conduit 96, air pumping means 93 being connected to a second port via conduit 98, passageway 90 being connected to a third port via conduit 100 and the fourth port being connected to the atmosphere (thus allowing for air passing through valve 94 to be vented to the atmosphere) via conduit 102. Controlling means 92 thus controls the supply of air to passageways 88 and 90 by controlling the opening and closing of the valve ports of valve 94.

The means for presetting the amount that piston 4 will move in piston container 2 preferably comprises a lever arm stop means 104 located adjacent to lever arm 84, said lever arm stop means 104 having lever arm stops 106 and said lever arm stop means 104 preferably being located adjacent to the end of lever arm 84 opposite to the end of lever arm 84 on which pivot 86 is located.

When air is pumped through conduit 96 to passageway 88, piston 78 is driven downward, thus driving piston rod 82 downward which causes the lever arm 84 to be pushed downward around the pivot 86. This movement of lever arm 84 downward in turn pulls piston rod 6 and thus piston 4 downward drawing driving solution from driving solution chamber 22 into the space formed above piston 4. This continues until the lever arm 84 hits the lever arm stop 106, which lever arm stop is preset to determine the movement of the lever arm 84 and thus the volume of driving solution drawn into piston container 2. When air is pumped through conduit 100 to passageway 90, piston 78 is driven upward, thus driving piston rod 82 upward which causes lever arm 84 to be pushed upward. This movement of lever arm 84 upward in turn pulls piston rod 6 and thus piston 4 upward, thus discharging driving solution from piston container 2. this continues until the lever arm 84 hits the other lever arm stop 106.

As seen in FIG. 2, the controlling means 92 preferably has a counter 108 that is set so that piston 4 is lowered and raised a preset distance a certain amount of times based on the supply of air to passageways 88 and 90.

The parts of the apparatus of this invention that are to be wetted with driving solution or sample solution are preferably made out of a material that is compatible with a wide range of driving and sample solutions, e.g., stainless steel, Teflon ®, glass, Kalrez ®, etc.

As beforementioned, in order to be able to vary the preset amount of sample solution by small increments, the diameter of the piston container 2 is preferably less than the diameter of the piston cylinder 10, more preferably is less than or equal to half the diameter of the piston cylinder 10, and most preferably is less than or equal to one-third the diameter of piston cylinder 10. The volume capacity of piston container 2 is also preferably less than the volume capacity of piston cylinder 10. In fact, piston container 2 is preferably a commercial syringe with a plunger, with the maximum volume capacity ranging from 50 microliters to 50 milliliters and more preferably from 1 to 10 milliliters.

Although this invention has been described with reference to its preferred embodiment, other embodiments can achieve the same results. Variations and modifications to the present invention will be obvious to those skilled in the art and it is intended to cover in the appended claims all such modifications and equivalents that follow in the true spirit and scope of this invention.

We claim:

1. A method of supplying a preset amount of sample solution to a liquid chromatographic column comprising the steps of:
    (a) moving a first piston which moves along the axis of a piston container sealingly contacting the side walls of said piston container a preset distance so as to draw a fixed amount of driving solution from the driving solution chamber of a piston cylinder into the piston container, thus displacing a second piston which moves along the axis of said piston cylinder sealingly contacting the side walls of said piston cylinder and dividing said piston cylinder into a sample solution chamber and a driving solution chamber, said displacement of said second piston serving to cause sample solution to be drawn from a sample solution reservoir into the sample solution chamber of the piston cylinder in a fixed amount equal to the fixed amount of driving solution drawn into the piston container;
    (a(1)) moving the first piston back to its initial position, the driving solution in said piston container being expelled to waste; and
    (b) pumping driving solution into said driving solution chamber in order to displace said second piston so that sample solution in the sample solution chamber is forced out of the sample solution chamber and onto said chromatographic column wherein step a and a (1) are repeated in sequence as many times as necessary until the desired amount of sample solution to be loaded onto the chromatographic column is obtained in the sample solution chamber.

2. The method of claim 1 further comprising the step of:
(c) interrupting the supply of the driving solution to the driving solution chamber once the sample solution in the sample solution chamber has been discharged onto said column and thereafter supplying driving solution directly to the column.

3. The method of claim 2 wherein the driving solution is supplied to the column and the sample solution is supplied to the column via a valve which is adjustable between a sample application position and an elution position.

4. A method of supplying a preset amount of sample solution to a liquid chromatographic column utilizing a system comprising:
(a) a piston container;
(b) a first piston adapted to move along the axis of said piston container sealingly contacting the side walls of said piston container;
(c) a first passageway for the introduction and removal of driving solution to and from said piston container;
(d) means for moving said first piston in said piston container;
(e) means for presetting the amount that said first piston will move in said container;
(f) a piston cylinder;
(g) a second piston adapted to move along the axis of said piston cylinder sealingly contacting the side walls of said piston cylinder and dividing said piston cylinder into a sample solution chamber and a driving solution chamber, said piston cylinder having two ends, a sample solution chamber end and a driving solution chamber end;
(h) a second passageway for the introduction and removal of sample solution to and from said sample solution chamber;
(i) a third passageway for the introduction and removal of driving solution to and from said driving solution chamber;
(j) a driving solution reservoir;
(k) a sample solution reservoir;
(l) a chromatographic column;
(m) pumping means for pumping driving solution from said riving solution reservoir into said driving solution chamber through said third passageway and for pumping a driving solution from said driving solution reservoir onto said chromatographic column;
(n) a first valve means (A) interconnecting said pumping means with said driving solution chamber; (B) interconnecting said driving solution chamber with said piston container; (C) interconnecting said piston container with said sample solution reservoir; (D) interconnecting said sample solution reservoir with said sample solution chamber (E) interconnecting said sample solution chamber with said chromatographic column; and (F) interconnecting said chromatographic column with said pumping means, wherein said pumping means is connected to said first valve means via a first conduit; said third passageway of said driving solution chamber is connected to said first valve means via a second conduit; said first passageway of said piston container is connected to said first valve means via a third conduit; said second passageway of said sample solution chamber is connected to said first valve means via a fourth conduit; said sample solution reservoir is connected to said first valve means via a fifth conduit; and said chromatographic column is connected to said first valve means via a sixth conduit, (a) filling the driving solution chamber of the piston cylinder with driving solution;
(b) setting the first valve means so that driving solution can pass from the driving solution chamber into the piston container;
(c) moving the first piston a preset distance from its initial position in said piston container so as to draw a fixed amount of driving solution from the driving solution chamber into the piston container thus displacing the second piston, said displacement of said second piston serving to cause sample solution to be drawn from the sample solution reservoir into the sample solution chamber of the piston cylinder in a fixed amount equal to the fixed amount of driving solution drawn into the piston container;
(d) adjusting the first valve means so that the pump means can pump driving solution directly to the driving solution chamber of the piston cylinder and sample solution can be discharged from the sample solution chamber onto the chromatographic column; and
(e) pumping driving solution into said driving solution chamber in order to displace said second piston so that sample solution in the sample solution chamber is force out of the sample solution chamber and onto said chromatographic column.

5. The method of claim 4 wherein in step a, the driving solution chamber is filled with driving solution by setting the first valve means so that the pumping means can pump driving solution directly to the driving solution chamber of the piston container and pumping driving solution into said driving solution chamber until said second piston is pushed to the sample solution chamber end of said piston cylinder.

6. The method of claim 4 wherein the system further comprises a waste container and means for connecting said waste container to said piston container and wherein prior to adjusting the first valve means in step d, there is a further step of:

c (1) expelling the driving solution in the piston container to said waste container by moving the first piston back to its initial position.

7. The method of claim 6 wherein steps c and c (1) are repeated in sequence as many times as necessary until the desired amount of sample solution to be loaded onto the chromatographic column is obtained in the sample solution chamber.

8. The method of claim 7 wherein said fifth conduit has a first check valve means which ensures that solution cannot flow into said sample solution reservoir and said means for connecting said piston container to said waste container comprises a seventh conduit, said seventh conduit having a second check valve means which ensures that solution cannot flow from said waste container to said piston container.

9. The method of claim 6 wherein prior to moving the first piston in step c, there is a further step of pumping driving solution directly to the chromatographic column.

10. The method of claim 4 wherein prior to moving the first piston in step c, there is a further step of pumping driving solution directly to the chromatographic column.

11. The method of claim 4 further comprising the steps of:
   (j) adjusting the valve means so that the pumping means can pump driving solution directly to the chromatographic column; and
   (k) pumping driving solution directly to the chromatographic column.

12. The method of claim 11 wherein the means for moving said first piston comprises a pneumatic system.

13. The method of claim 12 wherein the piston container has two ends, one end containing the first passageway for the introduction and removal of driving solution to and from the piston container and the second end being open to the atmosphere and wherein the pneumatic system comprises:
   an air cylinder;
   a third piston adapted to move along the axis of said air container sealingly contacting the side walls of said air cylinder and dividing said air cylinder into a first chamber and a second chamber;
   means to connect said third piston to said first piston through said open end of said piston container;
   a fourth passageway for the introduction of air to said first chamber of said air cylinder;
   a fifth passageway for the introduction of air to said second chamber of said air cylinder;
   means for supplying air into said air cylinder through said fourth and fifth passageways; and
   a second controlling means to control the supply of air to the fourth and fifth passageways, wherein in step c, the first piston is moved a preset distance by passing air into said fourth passageway of said first chamber of said air cylinder via said fourth passageway.

14. The method of claim 13 wherein in step c(1), the first piston is moved back to its initial position by passing air into said second chamber of said air cylinder via said fifth passageway.

15. The method of claim 14 wherein said means for supplying air into said air cylinder comprises:
   air pumping means; and
   a third valve means having valve ports, said third valve means (A) interconnecting said air pumping means with said fourth passageway; and (B) interconnecting said air pumping means with said fifth passageway, wherein said third valve means is connected to the air pumping means via a first pneumatic conduit, said third valve means is connected to the fourth passageway in the air cylinder via a second pneumatic conduit, said third valve means is connected to the fifth passageway in the air cylinder via a third pneumatic conduit, and a fourth pneumatic conduit connects said third valve means to the atmosphere, thus allowing for air passing through said third valve means to be vented to the atmosphere;
   said second controlling means controls the supply of air to the fourth and fifth passageways by controlling the opening and closing of the valve ports of the third valve means and wherein in step c, the first piston is moved a preset distance by pumping air through said third valve means into the first chamber of said air cylinder via said second pneumatic conduit and in step c (1), the first piston is moved back to its initial position by pumping air through the third valve means into the second chamber of said air cylinder via said third pneumatic conduit.

16. The method of claim 4 wherein the system further comprises stop means which prevent said second piston from contacting the sample solution chamber end of the piston cylinder, said stop means either being attached to said second piston or to said sample solution chamber end of the piston cylinder.

17. The method of claim 16 wherein there is a flexible sliding seal around the second piston that enables said second piston to sealingly contact the side walls of said piston cylinder and which sliding seal bends under pressure to allow driving solution from the driving solution chamber to enter the sample solution chamber when said stop means attached to aid second piston contacts the sample solution chamber end of the piston cylinder or when the second piston contacts the stop means attached to the sample solution chamber end of the piston cylinder.

* * * * *